(12) United States Patent
Clover, Jr. et al.

(10) Patent No.: US 6,660,204 B1
(45) Date of Patent: Dec. 9, 2003

(54) CUSTOM PROSTHESIS FABRICATION WITH IN SITU SHAPING OF INTERMEDIATE CASTING FORM

(75) Inventors: William M. Clover, Jr., Buffalo, MN (US); Anna M. Hendrickson, Buffalo, MN (US)

(73) Assignee: Otto Bock Orthopedic Industry, Inc., Plymouth, MN (US)

( * ) Notice: Subject to any disclaimer, the term of this patent is extended or adjusted under 35 U.S.C. 154(b) by 261 days.

(21) Appl. No.: 09/945,362

(22) Filed: Aug. 31, 2001

Related U.S. Application Data

(60) Provisional application No. 60/230,247, filed on Sep. 1, 2000.

(51) Int. Cl.[7] .................... B29C 33/38; B29C 39/02
(52) U.S. Cl. .................... 264/222; 264/220; 264/313; 264/319
(58) Field of Search .................. 264/219, 222, 264/313, 319, 220

(56) References Cited

U.S. PATENT DOCUMENTS

| | | | |
|---|---|---|---|
| 2,473,723 A | * 6/1949 | Nelson | 264/222 |
| 2,580,264 A | * 12/1951 | Wright et al. | 264/222 |
| 4,086,666 A | 5/1978 | Vaskys et al. | |
| 4,199,825 A | 4/1980 | Knoche | |
| 4,317,241 A | * 3/1982 | Knoche | 264/222 |
| 4,401,492 A | 8/1983 | Pfrommer | |
| 4,426,742 A | 1/1984 | Prahl | |
| 4,600,551 A | * 7/1986 | Erb | 264/222 |
| 4,701,230 A | 10/1987 | Loi | |
| 4,821,200 A | 4/1989 | Oberg | |
| 4,826,501 A | 5/1989 | Grundei | |
| 5,258,036 A | 11/1993 | Edenbaum et al. | |
| 5,352,307 A | 10/1994 | Wild | |
| 5,432,703 A | 7/1995 | Clynch et al. | |
| 5,527,359 A | * 6/1996 | Nakamura et al. | 623/7 |
| 5,798,062 A | 8/1998 | Thielbar | |
| 6,086,801 A | * 7/2000 | Eaton | 264/40.1 |
| 6,443,986 B1 | * 9/2002 | Malice, Jr. et al. | |

* cited by examiner

*Primary Examiner*—Allan R. Kuhns
(74) *Attorney, Agent, or Firm*—Faegre & Benson, LLP

(57) ABSTRACT

A process for fabricating a custom breast prosthesis or an intermediate casting form for a breast prosthesis, in which the task of creating the intermediate casting form is considerably simplified, and enables a shaping of the casting form, in situ.

24 Claims, 9 Drawing Sheets

CUSTOM PROSTHESIS FABRICATION WITH IN SITU SHAPING OF INTERMEDIATE CASTING FORM

This application claims priority from U.S. Provisional Application No. 60/230,247, filed Sep. 1, 2000, the entire content of which is hereby incorporated by reference.

TECHNICAL FIELD

This invention relates to custom prostheses, especially to custom breast prostheses. More particularly, the invention concerns providing and shaping an intermediate product used in prosthesis fabrication, namely, a casting form.

BACKGROUND

Post-mastectomy products include prefabricated breast forms, and custom breast prostheses. Custom prostheses are designed to conform to the chest wall of the patient, and thus provide a fit that looks and feels more natural as compared to non-custom products. Processes for fabricating custom breast prostheses are disclosed, for example, in U.S. Pat. No. 5,798,062 (Thielbar), U.S. patent application Ser. No. 08/955,535 filed Oct. 22, 1997, and U.S. patent application Ser. No. 09/174,199 filed Oct. 16, 1998 as a continuation-in-part of the '535 application. These processes require applying paste material (e.g., a dental alginate) substantially over the entire chest area in combination with wet plaster bandages. Then, a positive cast must be made, typically by spreading gypsum plaster over the inside of the negative cast. A breast form is sculpted using modeling clay placed on the positive cast. The sculpted clay is removed very carefully. A back mold is formed by applying a plaster or other paste material to the negative cast, to form on the back mold a positive replication of the chest area to which the custom prosthesis will be applied. Then, the sculpted formed clay mold is positioned on the back mold, the resulting structure is surrounded by a wall, and plaster poured to create a front mold. The front and back molds, when joined together, form a chamber into which a silicone gel is injected to form the custom prosthesis.

The preceding mold-forming process is time-consuming, cumbersome and unpleasant to the patient. The intermediate stages between the initial negative cast and the back mold reduce the degree of accuracy to which the back mold can replicate the thoracic (chest) area. Accuracy is further reduced by the tendency of the alginate to shrink when it dries. The initial negative cast frequently is not used immediately, but rather shipped to a fabrication center for use in making the positive cast and the front mold. This gives rise to the need to pack the negative cast in damp material and provide special expedited shipping and handling in an attempt to reduce the rate and amount of shrink due to drying out.

A further problem arises from the manner in which the clay breast form is provided, i.e., by sculpting a mound of modeling clay placed on the positive cast. When sculpting the clay, the clinician relies on a visible image, e.g., photograph of a remaining breast (reverse image), or the profile of an unsupported remaining breast provided by an unsupported positive cast. The patient may not be present during sculpting. If present, she can not inspect the form in situ, but instead must attempt to envision the appearance of the completed prosthesis based tab on the modeling clay form as it rests upon the positive cast.

SUMMARY OF THE INVENTION

The present invention provides a process for fabricating a custom prosthesis, in which the task of creating the intermediate casting form is considerably simplified, and enables a shaping of the casting form, in situ.

The primary source of these advantages is a thin-walled cup-like shell, substantially inextensible but elastic in that it tends to assume the cup-like shape when not subject to an external stress. Further, however, light pressure applied to the shell readily alters its shape. This balance of flexibility and formability is a result of the material involved, the shape of the shell, and the wall thickness. One material found well suited for constructing the shell is a semi-transparent, flexible polyethylene-based sheet material, available from American Plastics of Fort Worth, Texas under the brand name American Flexilene. Shells used in the fabrication of breast prostheses can have wall thicknesses ranging from about 1 mm to about 4 mm, with shells corresponding to larger cup sizes having the thicker walls.

The casting form is made of an elastomer; more particularly, a high viscosity polyvinylsiloxane putty. The putty is provided initially in two parts, combined by hand mixing of the parts in a 1-to-1 ratio to provide a putty mixture or matrix. The mixture has a setting or curing time on the order of seven minutes, and a working time (during which the putty matrix can be readily shaped, i.e., after which the matrix is largely permanently unalterable) of about three and one-half minutes. The curing time can be reduced, if desired, by the application of heat, even the relatively slight heat resulting from holding a hand or other part of the body against the matrix.

The casting form is made by mixing the parts of the putty, then without delay, filling the shell with the putty mixture, preferably to an excess of the matrix. Then, the filled shell is placed in a bra, and the bra fitted onto the patient, thus to press the putty mixture gently but firmly against the chest wall. Additional gentle pressure may be desirable, to ensure complete contact of a "back wall" of the matrix against the chest. After such pressure, however, the bra alone adequately maintains the shell/matrix position.

During the working time, the elastomeric matrix is pliable, and thus susceptible to shaping by hand as it cures. The shell, although resilient as noted above, is compliant in the sense that it tends to conform to the shape of the matrix. Thus, as the putty mixture is manipulated by hand into a new shape, the shell tends to conform to that new shape.

Simultaneously, the shell influences the shape of the matrix, by attenuating localized irregularities. For example, poking a thumb or finger into the matrix body away from the shell would tend to form a depression similar in radius to the thumb or finger. By contrast, pressure from the thumb or finger, when applied to the matrix through the shell, results in a much shallower depression with a much larger radius. In this manner, the shell "biases" any shaping of the shell/matrix combination away from local irregularities, toward smoother curves having larger radii. Such smooth, gradual contours are preferred, and are readily achieved even by relatively less skilled providers, when the shell/matrix combination is used to make the casting form. When cured, the elastomer is sufficiently hard (Shore A hardness of 25) to reliably maintain the desired shape.

Use of the shell in combination with the elastomeric putty matrix considerably simplifies fabrication of the casting form. The process no longer requires the application of a dental alginate and wet plaster bandages to the chest to form a negative cast, nor is the subsequent positive cast required. There is no need to sculpt a breast form from modeling clay, or to place the resulting form over the chest wall at the area of the scar. There is no need to form a separate back mold of dental alginate or other paste material.

The shell/matrix combination results in a more accurate casting form. The alginate or other paste material used in the conventional process tends to shrink when it dries, giving rise to the need for maintaining alginate casts and forms damp, or suffer the consequences of shrinkage. The elastomeric putty used in combination with the shell does not shrink as it cures, and consequently provides a closer replication of the chest wall, accurately reproducing incision marks, scar tissue, and soft tissue folds. The cured matrix can be shipped to the fabrication center at the fitter's convenience. No expedited handling is required. The resulting prosthesis assumes a more conforming, more comfortable fit.

A salient feature of the present invention is the degree to which the patient can participate in the shaping of the casting form. The modeling clay breast form of the conventional process typically is constructed in the absence of the patient, based on measurements and photographs or other visual aids. In the present process, the shell/matrix combination is shaped in situ while the putty mixture cures. Not only is the patient present during shaping. But by virtue of the in situ shaping, she can participate in "real time" fashion. Held against the patient's chest during shaping, the casting form provides a direct indication of the appearance of the resulting prosthesis, since the casting form is in the position to be occupied by the completed prosthesis. The provider (e.g., prosthesis specialist) and patient can work together to adjust and refine the shape of the casting form, again with the form in the position of intended prosthesis use. Thus given an active role in the shaping of the casting form, the patient is more confident that the resulting prosthesis will more accurately reflect her preferences.

An embodiment of the present invention can include a method for fabricating an intermediate casting form for a breast prosthesis for a particular patient. This method could include providing a shell having a cup-like shape and adding an impression material into the shell. The shell containing the impression material can be placed into a cup of a bra that corresponds to where the breast prosthesis is desired. The bra can be fitted onto the patient. The impression material can be allowed to begin to set when contacting a chest wall portion of the patient. The shell and impression material can be removed from the bra before the impression material is permanently unalterable, wherein the shell and impression material together have an initial shape. After the step of removing shell and impression material, the initial shape can be manually altered to make an intermediate shape by applying pressure to the impression material before the impression material is permanently unalterable.

Still another embodiment of the present can include a method for fabricating a breast prosthesis for a particular patient: This method can include providing a shell having a cup-like shape and adding a impression material into the shell. It can also include placing the shell containing the impression material into a cup of a bra that corresponds to where the breast prosthesis is desired and fitting the bra onto the patient. The impression material can be allowed to begin to set when contacting a chest wall portion of the patient. The shell and impression material can be removed from the bra before the impression material is permanently unalterable wherein the shell and impression material together have an initial shape. After the step of removing shell and impression material, the initial shape can be manually altered to make an intermediate shape by applying pressure to the impression material through the shell.

The impression material can be allowed to set further when substantially in the intermediate shape to create the intermediate casting form for the breast prosthesis. A mold may be formed using the intermediate casting form, and filed with a prosthesis material to form the breast prosthesis.

DETAILED DESCRIPTION OF PREFERRED EMBODIMENTS

Preferred embodiments of the invention now will be described, primarily with respect to a breast prosthesis.

Nonetheless, it should be recognized that other prostheses can be fabricated and other fabrication methods can be employed in accordance with the principles disclosed.

Figure 1:
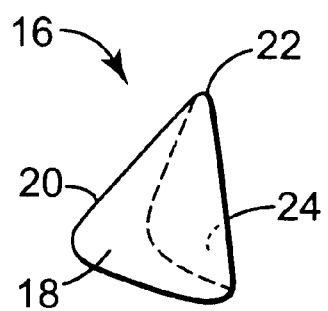
FIG. 1 is a perspective view of a shell, which can be a useful part of the present invention.

FIG. 1 shows a flexible shell 16 having a cup-like shape corresponding at least approximately to a predetermined breast size and shape. If desired, shell 16 is provided as one of a set of several such shells, to provide different choices in shape, and within each shape, several different choices as to size. Shell 16 has an outside surface 18, a shell wall 20 with an edge 22 that defines a shell opening, and an inside surface 24 visible through the opening. Shell 16 preferably is formed of a polymer, e.g., a semi-transparent, flexible, polyethylene-based sheet material available from American Plastics of Fort Worth, Tex. under the brand name American Flexilene. Other polyolefin-based materials could be used as could other polymeric materials that provide the noted desired properties.

Shell 16 is substantially inextensible, e.g., is not an elastomer and/or does not stretch elastically to two-hundred percent (200%) and, more preferably, not to one-hundred fifty percent (150%). The shell is flexible and conformable, tending to assume the shape shown in FIG. 1 when not subject to external stresses. At the same time, the shape of the shell can be changed by applying light pressure (preferably light pressure applied by the hand(s) of an adult person), most conveniently in directions perpendicular to shell wall 20. The thickness of shell edge 22 and wall 20 ranges from about 1 mm to about 4 mm, though a greater thickness may be preferred with larger sized shells. In any event, the wall thickness is selected to achieve a satisfactory compromise between two competing functions, compliance and smoothing, as discussed later. Two different shell types/sizes could, for example, be used or chosen from a particular patient. A first shell type could be shaped to better allow for the formation of a breast prosthesis that matches a natural breast of an older woman, whereas a second shell type could be shaped to better allow for the formation of a breast prosthesis that matches a natural breast of a younger woman.

Although selecting shell 16 is an early step, an important initial step in the fitting process is to ensure that the patient has a properly fitting bra. The bra is an important component in shaping and evaluating the appearance of an intermediate casting form. The casting form is used later in prosthesis fabrication. A later section, entitled "Bra Fitting," describes this in more detail.

Then, the correct size and shape of the shell are selected. In the case of a single mastectomy, selection can begin with a visual comparison with the remaining breast. Next, shell 16 is placed in the bra and viewed by the clinician and the patient, either to confirm that the appropriate size and shape have been selected, or to try an alternative shape or size.

Figure 2:
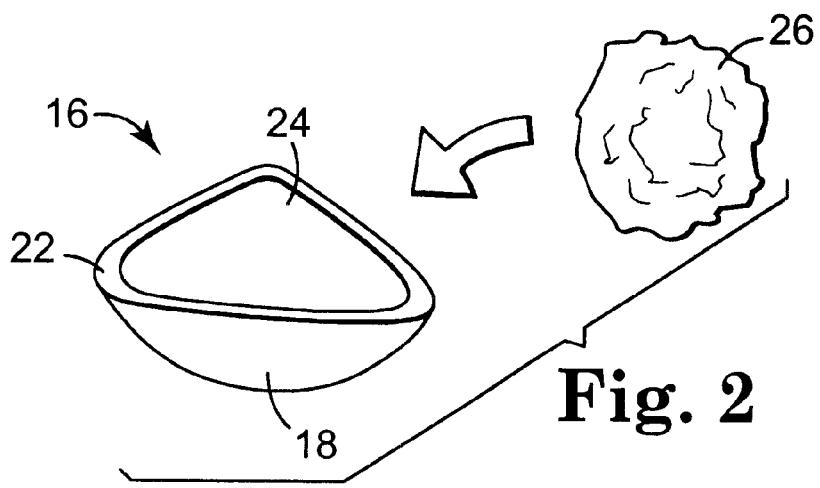
FIG. 2 is a perspective view of the shell shown in FIG. 1 with an impression material being moved toward the shell.

As illustrated in FIG. 2, the next step is to provide or form an elastomeric impression material, e.g., a putty matrix. (supplied by Matrics Inc., 8780 Jefferson Highway, Osseo, Minn. 55369; product number EXP-C-K2 Impression Putty). This preferred material is a polyvinylsiloxane putty. It can be prepared using two (e.g., precursor) parts, preferably of different colors to provide a visual indication (a single intermediate color) when a sufficient mixing has occurred. Mixture of the two parts initiates a curing process that can last from approximately three to ten minutes, or more preferably lasts about seven minutes. The initial half (about three and one-half minutes) of the curing time constitutes a working time in which the elastomeric putty mixture or matrix, while having a high viscosity, is pliable and easily shaped by hand. When curing is complete, the elastomer preferably hardens to a Shore A hardness of about 25 and thereafter retains its shape, i.e., the elastomer is permanently unalterable.

Other elastomers, including thermosetting, thermoplastic, and other non-thermal-cured elastomers, can be used in place of the described polyvinylsiloxane. I.e., such other available or later developed materials would provide the flow property (to conform to the chest wall), formability, property, set-up property (e.g., cure), and/or the release property provided by the polyvinylsiloxane.

Figure 3:
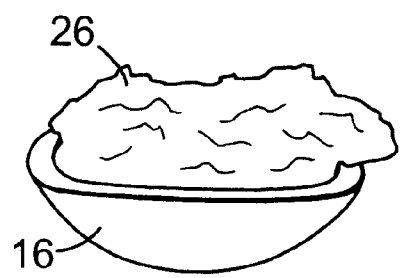
FIG. 3 is a perspective view of the impression material and shell shown in FIG. 2, with the impression material being within the shell.

As shown in FIGS. 2 and 3, impression putty matrix 26 is loaded into shell 16, pressed into the shell to ensure the shell is completely filled, and preferably overfilled to leave an excess of about ¾ inch (18 mm) extending out of the shell beyond the shell opening as shown in FIG. 3. When the shell is filled, the shell/matrix combination is placed on a soft support such as a towel or cushion, to avoid any flattening which might occur if the shell/putty were placed on a table or other hard surface.

Figure 4:
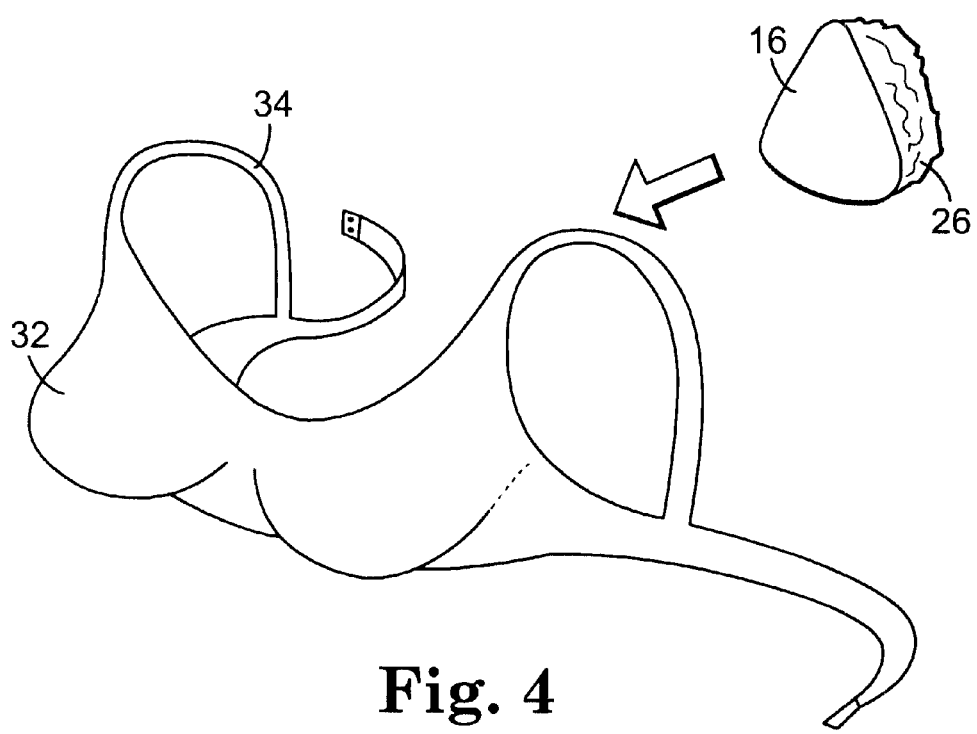
FIG. 4 is a perspective view of the impression material and shell from FIG. 3 being moved toward a cup of a bra.

The shell/putty combination is inserted into a pocket or cup 32 of the bra 34 (FIG. 4), with shell 16 facing in an anterior direction against the bra, and the impression putty mix, particularly the excess, facing in a posterior direction. Then, as the bra is placed onto the patient, it tends to push the shell/putty assembly backwardly against the chest wall, so that the exposed impression putty matrix conforms to the chest wall. At this stage, some backward pushing by hand may be necessary to ensure that the impression putty is fully contiguous with the chest wall, after which the bra alone is sufficient to maintain the assembly in place. Thus, the shell/putty assembly is maintained in situ, i.e. in the position in which the patient expects to wear the breast prosthesis. The elastomer, when properly pushed against the chest wall, forms an accurate impression of incision marks, scars and soft tissue folds.

Figure 5:
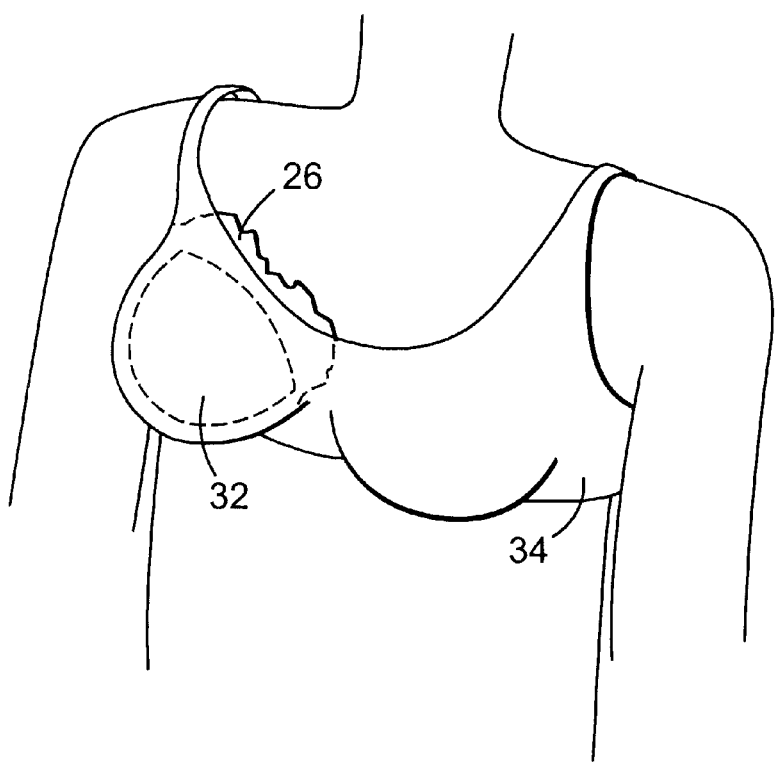
FIG. 5 is a perspective view of the impression material and shell from FIGS. 3 and 4 being in position within the bra cup of FIG. 4 and with the bra on a female.

In FIG. 5, bra 34 is seen to maintain the shell/putty assembly in situ. At this point, it may be desirable to remove some of the excess putty from around bra 34, by wiping it away with the fingers, or a towel or cloth. In any event, the shell/putty assembly, based on the initial selection of shell 16, at least approximates the desired size and shape of the prosthesis to be fabricated. Further during the working time, the elastomeric putty mixture remains pliable, and can be readily shaped manually, e.g., by hand, to form a custom shape that closely approximates the sound side, or natural breast.

As noted above, shell 16 has a wall thickness selected to provide a balance between two competing functions: compliance and smoothing. Compliance refers to the tendency of shell 16 to conform to impression matrix 26 as the matrix is shaped by hand. Such shaping typically elastically deforms shell 16, creating an elastic restoring force in the shell that, in the absence of the matrix, would cause the shell to return to its normal, unstressed shape. Matrix 26, due to its high viscosity, keeps its shape in spite of the elastic restoring force in the shell. A thinner shell wall increases the compliance of the shell.

Figure 6:
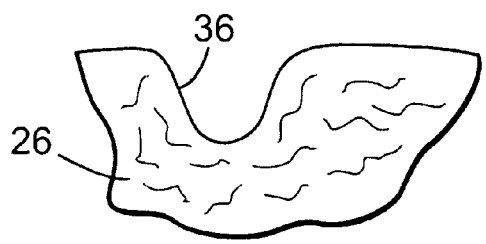
FIG. 6 is a schematic view of a depression formed in impression material with a push of a thumb, finger or similarly sized object when such push is not applied to the impression material through the shell.

Smoothing capability refers to the tendency of shell 16 to attenuate local surface discontinuities such as depressions with small radii, when the shell and matrix are being shaped. For example, FIG. 6 illustrates a depression 36 formed by poking matrix 26 with a thumb, finger or similarly sized object at a location remote from wall 20. The indentation has a small radius of curvature, typically less than about one-half inch.

Figure 7:
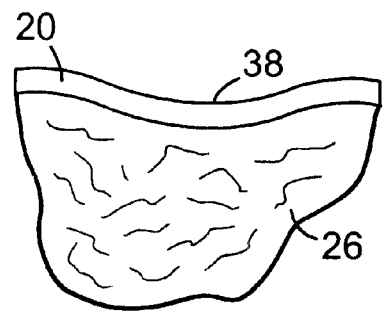
FIG. 7 is a view of a schematic view similar to that shown in FIG. 6, but with the push being applied through the shell.

FIG. 7 illustrates a depression 38 formed by applying the same pressure with the same object to matrix 26, this time through shell wall 20. As compared to depression 36, depression 38 is more shallow, and has a much larger radius of curvature. The smoothing or attenuating quality of shell 16 increases with the thickness of wall 20. This smoothing characteristic enhances hand shaping of the shell/matrix assembly, producing gradual contours substantially free of localized depressions and other surface discontinuities.

Figure 8:
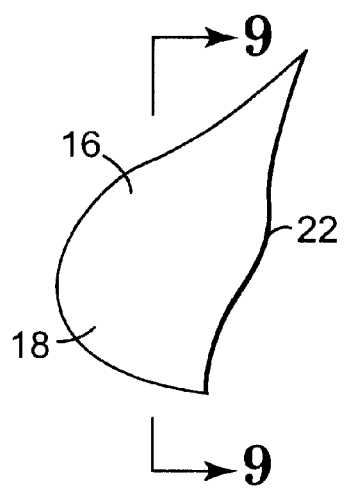
FIG. 8 is an initial profile view of the shell and impression material before hand shaping.
Figure 10:
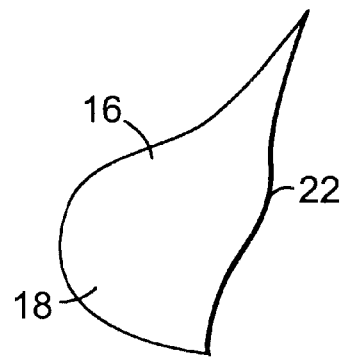
FIG. 10 is a profile view similar to FIG. 8, but following handshaping to reduce the vertical dimension and increase the horizontal dimension of the shell and impression material.
Figure 9:
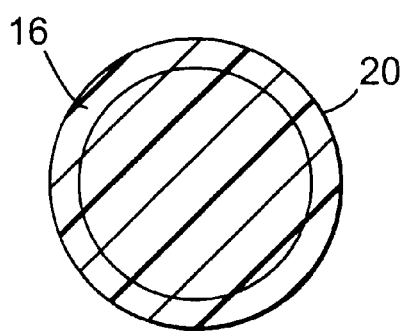
FIG. 9 is a vertical sectional view from FIG. 8.
Figure 11:
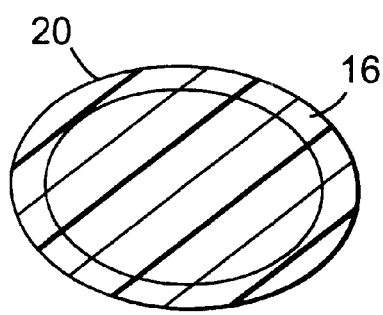
FIG. 11 is a vertical sectional view of FIG. 10.

FIGS. 8–11 illustrate an example of shell/matrix shaping. It is understood that shaping occurs with the shell/matrix supported against the chest wall by bra 34, although the bra and patient are not illustrated in these figures. FIGS. 8 and 9 illustrate an initial profile view and a vertical sectional view, respectively. FIGS. 10 and 11 correspond to the views of FIGS. 8 and 9, respectively, after the shell and matrix have been hand shaped to reduce the vertical dimension and increase the horizontal dimension of the shell and matrix, providing the more elliptical cross-section shown in FIG. 11.

When initially positioned against the chest wall, matrix 26 conforms to the chest wall and replicates such details as incision marks, scars, and soft tissue folds. Because there is no shrinkage of the matrix as it cures, the fully cured matrix accurately replicates the chest wall, specifically in producing a negative image.

Figure 12:
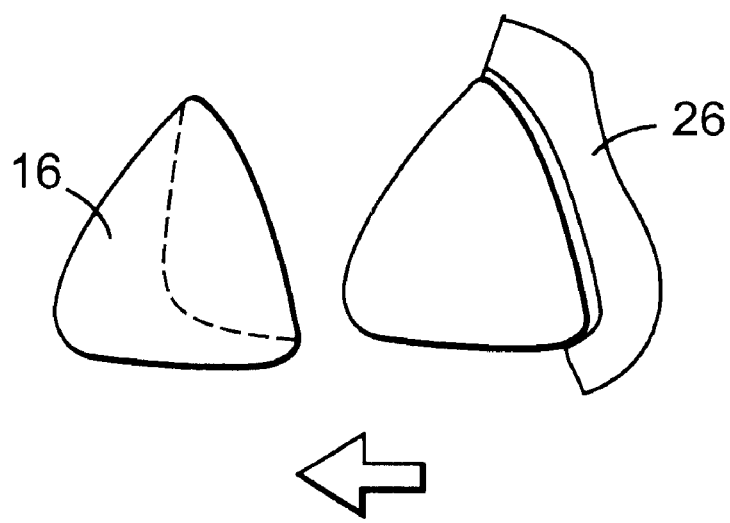
FIG. 12 is a perspective view of the shell and impression material shown in FIG. 5 (after removal from bra and after curing of the impression material to a cured matrix), with the shell being removed from the cured matrix.

When the matrix has cured, the patient may wish to evaluate the appearance, again with the shell and matrix in situ. If the appearance is satisfactory, the shell and cured matrix, which together provide the intermediate casting form, are removed from the bra. This is the only intermediate casting form required, because the shell when supported by the matrix provides the forward image, and the back wall of the matrix provides the negative chest wall image. Thus capturing the positioning relationship of the front shape and the rear surface. At this point, shell 16 is removed from matrix 26 as shown in FIG. 12, leaving matrix 26 ready for further processing in fabricating the breast prosthesis. The placement of the nipple/areola are marked on the surface of the matrix with a marking pen. Typically, this involves sending the cured matrix and the fitting bra to a fabrication center, along with the patient's choices of skin color, and nipple/areola color, size and shape. Before shipping, matrix 26 is marked for the intended nipple/areola location, and further marked with any trim lines.

Figure 13:
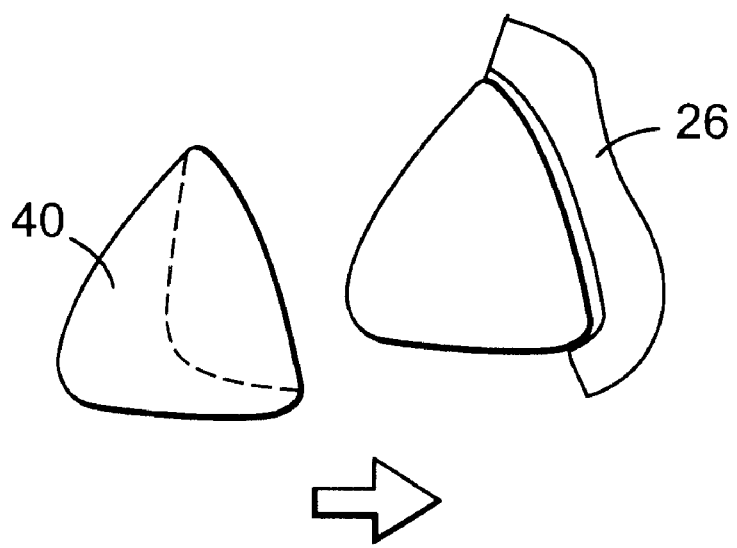
FIG. 13 is a perspective view of a duplicate shell of the same shape and size as the shell shown in FIG. 12 is placed onto the cured matrix.
Figure 14:
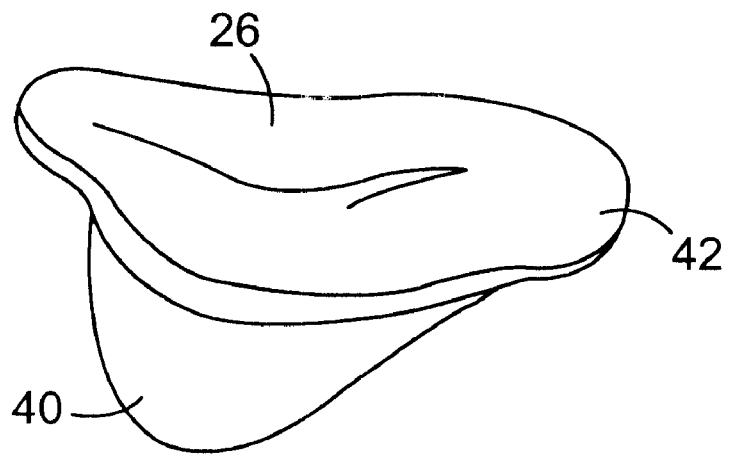
FIG. 14 is a perspective view of the shell/matrix combination shown in FIG. 13, with a back wall facing upward.
Figure 15:
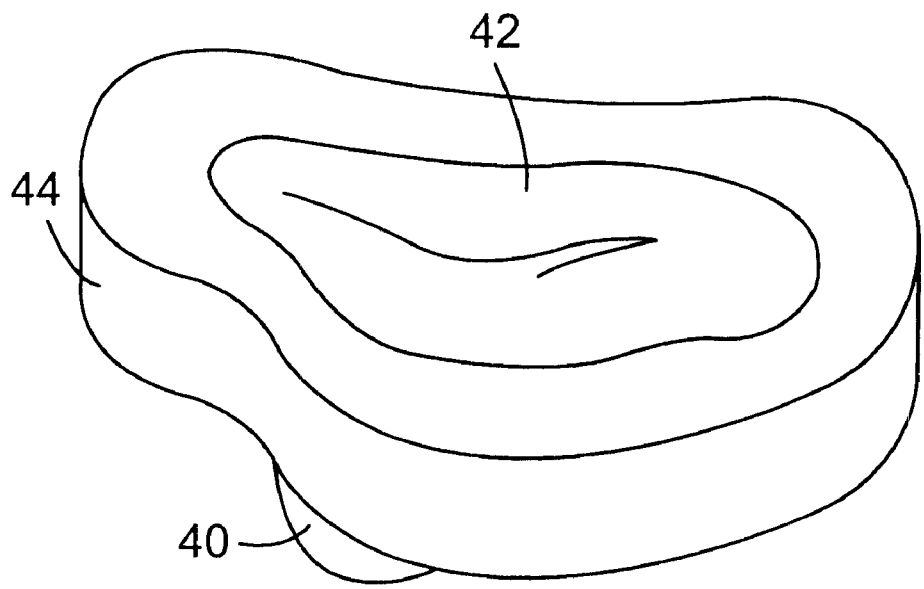
FIG. 15 is a perspective view of the shell/matrix augmented with modeling clay.

At the fabrication center, a duplicate shell 40 of the same shape and size as shell 16 is placed onto the elastomeric matrix, as seen in FIG. 13. The shell/matrix combination, with a back wall 42 facing upward as shown in FIG. 14, is placed on an annular support 46 (FIG. 16), and augmented with modeling clay as shown in FIG. 15. This provides a rim 44 surrounding the matrix and extending outwardly from the matrix approximately one and one-half inches (3.8 cm).

Figure 16:
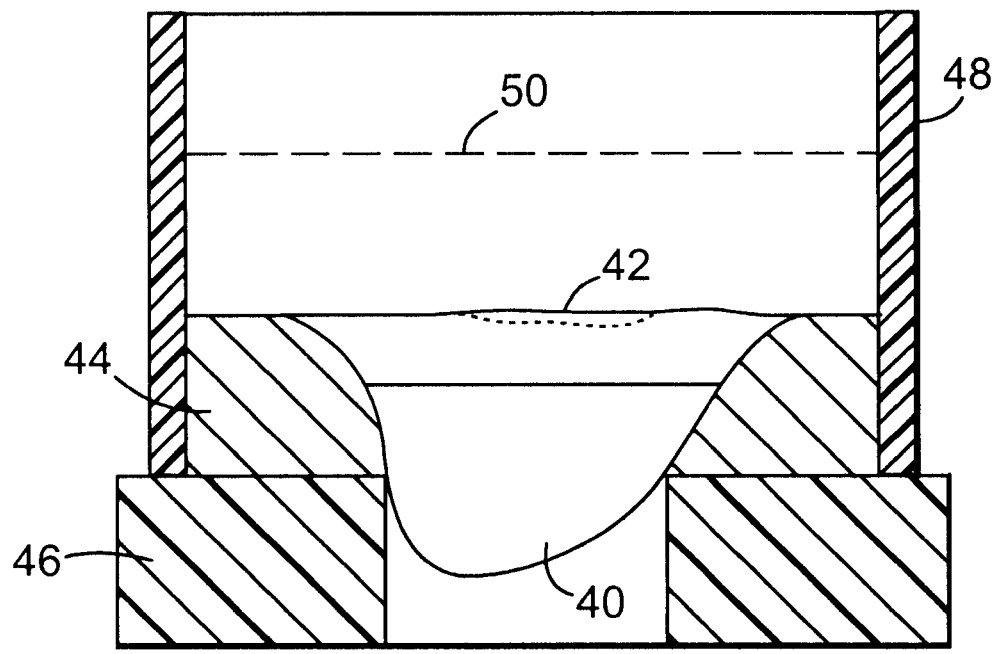
FIG. 16 is a side view of the shell/matrix in an annular support.

Next, with the augmented combination on annular support 46 as shown in FIG. 16, a casting wall 48, formed, e.g., of polyethylene or other flexible material, is positioned against rim 44 in surrounding relation to the rim, to provide a receptacle for pouring plaster to a level indicated by the broken line 50. Wall 48 extends approximately three inches above the modeling clay. Plaster is poured after spraying wall 42 and rim 44 with a mold release agent.

Figure 17:
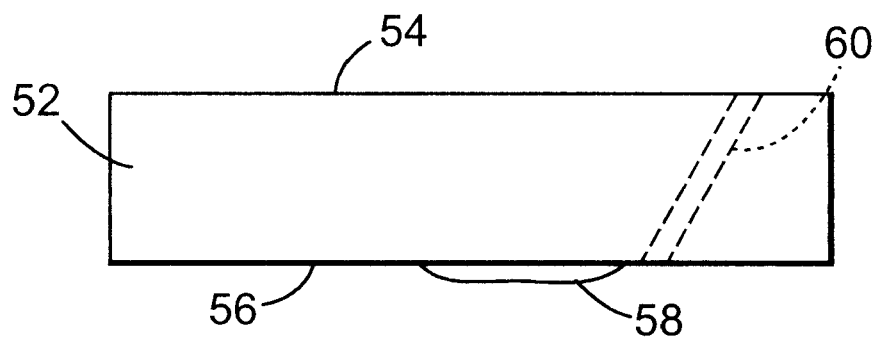
FIG. 17 is a side view of clay or plaster shown in FIGS. 15 and 16 hardened forming a back mold section.

The plaster hardens to form a back mold section 52 as shown in FIG. 17. A back surface 54 of the mold, i.e., the surface on top when the plaster is poured and sets, is substantially planar. A front surface 56 of the mold section replicates back wall 42 of the casting form, thus providing a positive image of the chest wall as indicated schematically by a relief 58. A hole 60 is formed through the back mold section, to accommodate injection of a silicone rubber in gel form as discussed below, and to facilitate evacuation of air during injection. Two holes may be formed, if desired.

Alternatively, the injection hole can be directly under the nipple/areola, which eliminates having to patch the back side after fabrication. With this approach, the nipple/areola can be attached after the breast is made so it now makes a nice cover for the injection hole.

Figure 18:
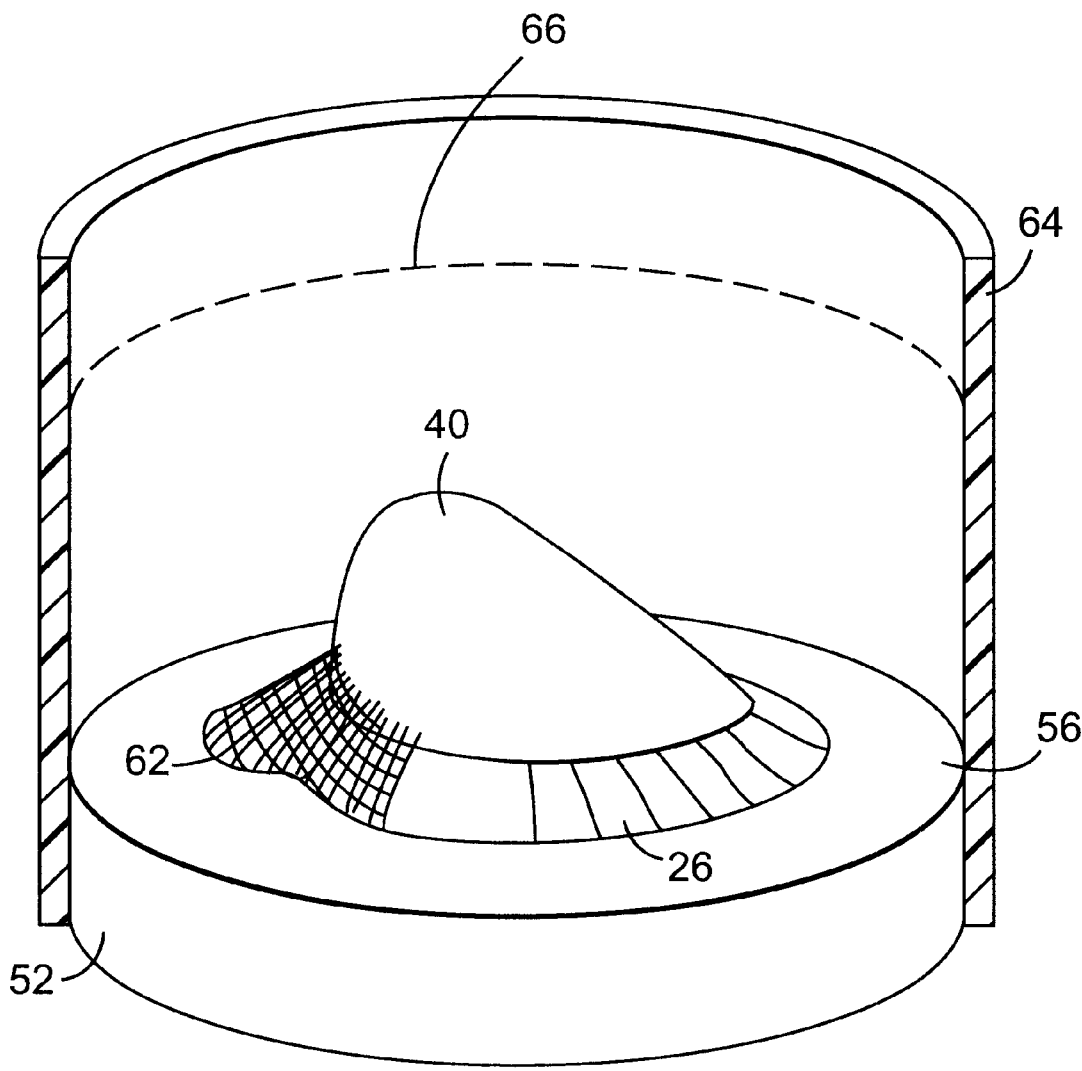
FIG. 18 is a perspective view of the back mold section, with the back mold section being turned over to rest on a back surface.

With back mold section 52 turned over to rest on back surface 54 as shown in FIG. 18, modeling clay is applied between shell 40 and the elastomeric matrix, to create a smooth transition 62. Next, the back mold section is surrounded by a casting wall 64. The back mold section is sprayed with a mold release agent. Plaster is poured to a level represented by the broken line 66, typically to a depth of about three inches.

Figure 19:
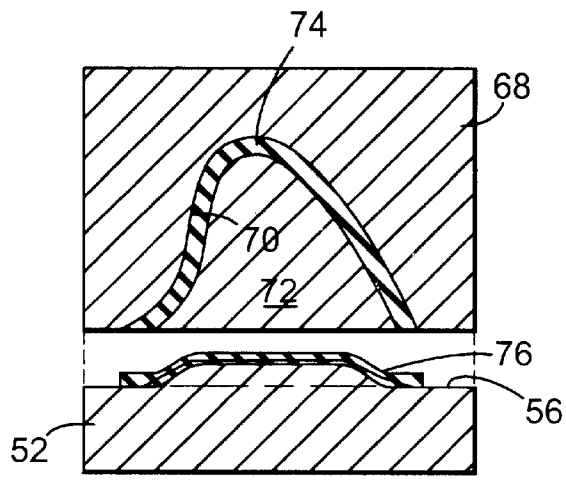
FIG. 19 is a side view similarly to FIG. 18, but with the shell/matrix casting form being removed, leaving a mold consisting of back mold section and a front mold section.
Figure 20:
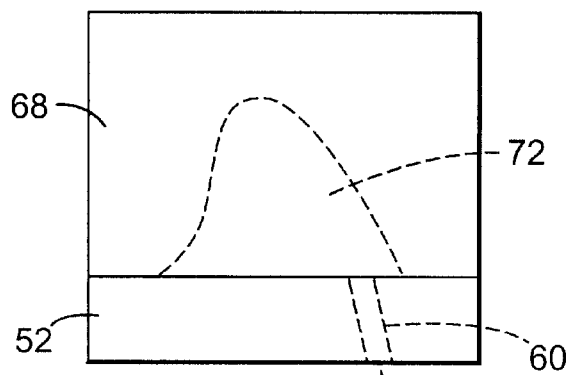
FIG. 20 is a side view similar to FIG. 19, but with the two mold section brought together.

After the plaster hardens, the shell/matrix casting form is removed, leaving a mold consisting of back mold section 52 and a front mold section 68 (FIG. 19). An inside wall 70 of front mold section 68 defines a chamber 72. The inside wall is sprayed with a release agent, then coated with a thin (e.g., 1/16 inch or 1.5 mm) layer 74 of silicone, more particularly a silicone layer tinted to match the skin color previously selected by the patient. A similarly thin silicone layer 76 is applied over front surface 56 of mold section 52. As a result, bringing mold sections 52 and 68 together, as indicated in FIG. 20, seals chamber 72. The mold sections may need to be smoothed (sanded) before applying the silicone layers.

Figure 21:
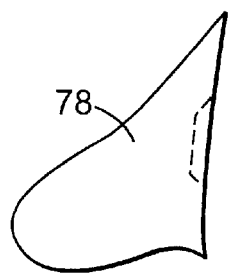
FIG. 21 is a side view of a breast prosthesis made within the molds shown in FIG. 20.

Before mold sections 52 and 68 are brought together, the cavity in mold section 68 is substantially (about two-thirds) filled with a suitable silicone gel material. Then, with the chamber sealed, more of the silicone gel is added, by injection into the chamber through is hole 60. When chamber 72 is filled, hole 60 is sealed, and the mold sections are placed within an oven to bake the silicone at temperatures in the range of from about 90 degrees C. to about 200 degrees C., for a time ranging from about 3 hours to about 6½ hours, depending on the baking temperature and the size of the prosthesis. After baking, and after a sufficient cooling of mold sections 52 and 68, the sections are separated and the silicone breast prostheses 78 (FIG. 21) is removed. At this point there is a hole through silicone layer 76, through which the silicone gel was injected into chamber 72, wherein this hole can be filled and the outside surface of layer 76 is touched up, with the same silicone material used in forming layers 74 and 76. If the earlier noted alternative approach of placing the injection hole below where the nipple/areola is to be placed, the placement of nipple/areola simplified this part of the process.

Preferred silicone formulations for layers 74 and 76 include liquid injection molding silicone elastomers available from Nusil Technology of Carpenteria, Calif., and designated as MED10-6400, MED10-6640, and LSR4-5805. Suitable silicone formulations for the silicone gel injected into chamber 72 also are available from Nusil Technology, designated as MED12-6301, GEL-9980, and GEL-8150.

As an alternative to the steps shown in FIGS. 16–18, mold sections 52 and 68 are formed without plaster, and without the need to provide walls 48 and 64. In particular, back mold section 52 is formed by applying (spraying) a urethane foam onto surface 42 and rim 44 while they are at rest on support 46 as shown in FIG. 16. The urethane foam conforms to the shape of surface 42, tends to rise and is self-contained, eliminating the need for wall 48. Then, with the back mold section turned over as shown in FIG. 18, and following formation of transition 62 as before, urethane foam is sprayed onto front surface 56, matrix 26, transition 62 and shell 40. Again, because the foam is self-supporting, no wall 64 is required. The urethane mold sections cure in less time (e.g., 30 to 45 minutes) than is required for their counterpart plaster mold sections to dry (e.g., 24 to 26 hours).

Figure 22:
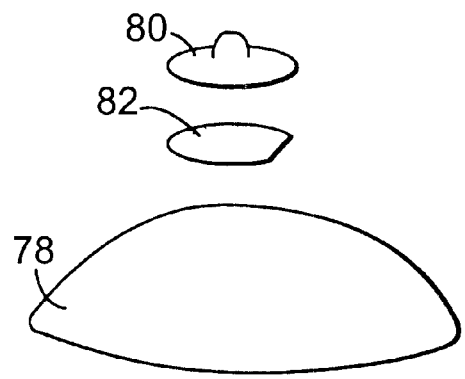
FIG. 22 is a side view of the breast prosthesis shown in FIG. 21, with a nipple/areola combination being applied to the prosthesis.

If the nipple/areola are not applied at the fabrication due to the fitter and patient desiring to place them after fitting, the silicone prosthesis is returned to the fitting center, along with a nipple/areola 80 having the color and shape selected earlier by the patient. At the fitting center, the provider and patient can inspect the prosthesis, and determine the correct location for the nipple/areola. Then, the nipple/areola combination is applied to the prosthesis, preferably using a pressure sensitive adhesive, or alternatively a self-adhesive backing 82 as indicated in FIG. 22. In an alternative approach, nipple/areola 80 is applied at the fabrication center.

Figure 23:
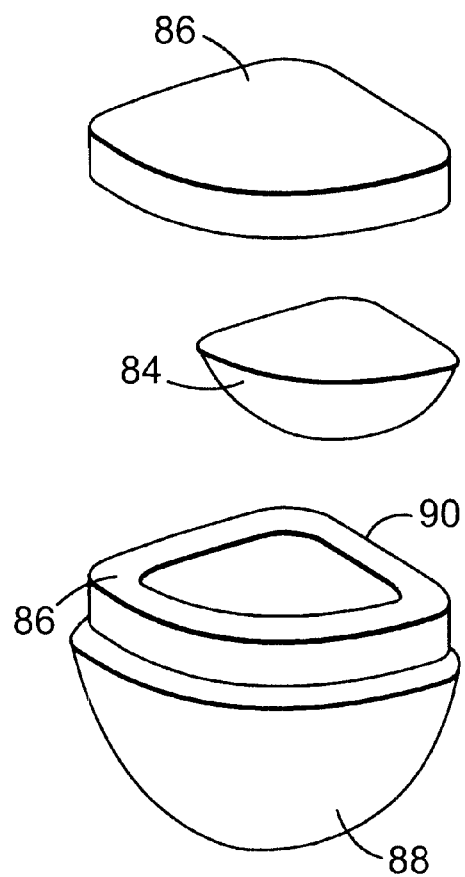
FIG. 23 is a perspective view of an alternative embodiment in which an intermediate casting form incorporates an inert filler material.

In an alternative embodiment process, the intermediate casting form incorporates an inert filler material, e.g., a clay, putty, soft foam or rigid foam, as indicated at 84 in FIG. 23. The alternative process is similar to the aforementioned process, in that a matrix 86 (like matrix 26) is formed by mixing two parts of a high viscosity polyvinylsiloxane putty material, then loaded into a flexible, thin-walled shell 88. However, matrix 86 is applied at first, only to form a layer 90 approximately one-half inch (12 mm) thick inwardly of the inside surface of the shell. Filler 84 then is inserted into the resulting opening, and further matrix material is packed into the opening to surround the filler material. As before, the shell is overfilled, to leave an excess of the elastomeric matrix material for pressing against the chest wall (forming at least a partial flange of elastomeric matrix material adjacent the breast-like created by the bra cup).

This process is particularly well suited for fabricating larger prostheses. The filler material is selected to reduce the weight of the casting form. The mass of matrix material also is reduced, which increases the curing time. The capacity for shaping and accurately capturing the chest wall image remains intact, because the filler material is completely surrounded by the elastomeric matrix.

Further in accordance with the present invention, the flexible, thin-walled shells can be employed in the fabrication of prostheses for other parts of the body. For example, a shell that approximately replicates the front part of the foot, including the toes, can be used in the fabrication of a prosthesis extending forwardly from an area of the foot between the ankle and toes. Prostheses to replace missing fingers, or a complete hand, likewise may be fabricated using a thin-walled shell and elastomeric matrix according to the present invention.

In all cases, the wall thickness of the shell is selected to provide a compliant shell that conforms to the matrix during shaping, yet attenuates shaping to provide more gradual curvature to avoid formation of small indentations and other surface discontinuities, all while facilitating shaping the shell and matrix while they occupy the expected location for the prosthesis. The patient's ability to determine a satisfactory shape is considerably enhanced, as is the ability of the clinician to form the matrix and shell into the selected shape. Processing time and cost are reduced by eliminating the need for providing preliminary castings, and for sculpting the clay model, and by the fact that a single casting form can be used to provide both mold sections. (This allows the patient to see a very close approximation of what they will receive as a finished prosthesis—the variables would be color and weight.)

Other embodiments or variations of the above-described embodiments are contemplated by the inventors. For example, rather than using a bra, the inventive method could use a cup designed to replace the function of the bra in terms of the inventive method.

BRA FITTING

During the initial consultation with a client, measure her to ensure her bra fits properly. It is best to take these measurements while the client is wearing a bra.

Determining bra size involves measuring around her bra band. If this measurement is an odd number of inches, add 5. If this measurement is an even number, add 6. If this measurement is 33 inches or more, add only 3 inches.

In determining cup size when the client had a bilateral mastectomy, she should choose the cup size she wore prior to her surgery. Or, she can opt to go one cup size larger or smaller. Place foam forms of her desired size (if available) inside the bra and check the fit and size. For unilateral mastectomy clients, first measure from the sternum over the fullest part of the remaining breast to the spine. Second, double this measurement. Do not round up or down unless the resulting measurement is a fraction, in which case it should be rounded up. For example, a 17½" measurement× 2=35" cup measurement. Or, a 18½" measurement×2=37" cup measurement. Then, subtract (i.e., determine the difference between) the band measurement from the cup measurement, which corresponds to an industry-set cup size. The following is the difference-cup size correlation: 0"=AA, 1"=A, 2"=B, 3"=C, 4"=D, 5"=DD, 6"=DDD. Remember that the resulting bra size is based on most manufacturers' measurements. Use this number as a starting point, but make adjustments as needed (e.g., adjusting the straps, using first and last hooks). Refer to the later-described tips to determine if the bra is still too big or too small, in which case a different band and/or cup size should be considered.

Trying on the bra can includes several steps. First, help the client into her bra by holding the shoulder straps up for her to slip her arms through. Second, hook the back while she bends forward so that her natural breast will fill the bra cup. Third, the bra should be hooked so it fits comfortably and snugly. It is recommended to use the middle hook. Fourth, teach the client how to bring breast tissue up into the cup so that the nipple is at the center of the seam. Fifth, adjust the strap so that the breast is held securely and at a comfortable level. Sixth, place a sample prosthesis (or her current form) in the bra cup to balance her figure, especially if it is necessary to keep the center of the bra at midline.

Regarding checking the fit, a properly fitted bra is essential to a properly fitted breast prosthesis. The Custom Expressions™ prosthesis is created to fit in many standard bras. Therefore, mastectomy bras and/or bra extenders should not be used therewith. To check fit, first view the client from all angles, checking the shape and symmetry. Next, if the fit is good, let the client check too. Have her look into the mirror, not down. If the client is bilateral, check the proportion of her breasts to her hips to see if she looks top-heavy or bottom-heavy. Ask the client her opinion. She may want to go up or down from her original size.

The bra is too small if (a) the shoulder straps cut into her shoulders, (b) breast tissue is not contained in the cup, (c) tissue bulges in underarm area, (d) fabric is tight and binding, or (e) the band creates an indentation in the skin on the back or side.

The bra is too large if (a) fabric wrinkles or puckers in the cup area, (b) the panel under the arm seems loose, or (c) the bra rides up in back.

Features of the bra with good support and comfort include (a) comfortable shoulder straps with wide straps or cushion straps often being best, (b) well-structured or reinforced cups, (c) wide lower band, (d) good coverage, (e) underwire support and/or well-structured seamed support, and (f) wide band around and in back, especially with larger sizes.

The shape of the cup will affect the shape of the natural breast and the prosthesis. For instance, women who wish to create an image of round or teardrop shaped breasts may want to consider an underwire bra. Keep in mind, however, that some women report discomfort with underwires following surgery.

Different bra designs have different effects. Some bras that are not recommended for use with Custom ExpressionsTM custom breast prostheses (from Otto Bock Health Care, Plymouth, Minn.) include (a) bras with seams running horizontally across the middle of the cups, (b) bras having a three-piece design have again a horizontal seams with a vertical seams coming up from the bottom middle of the cups and meeting with the horizontal seams, (c) demi cups/push-up bras, and (d) padded cups which often include an insert of fiberfill material that can interfere with the placement of the prosthesis.

Recommended bras for a Custom ExpressionsTM prosthesis include (a) bras with the princess seams, which run diagonally over the cups and may work best with rounder breast shapes, (b) bras with seams similar to princess seams but more vertical, (c) seamless bras, (d) bras with lightly lined cups, i.e., a minimum amount of fiberfill lining, and (e) underwire bras.

A bra-fitting check list includes the following. Bras with A or B cup sizes may not have the stitching or sturdy straps necessary to hold the prosthesis in place; therefore, check to durability of the bra being considered. When working with a full-figured client, take special care that the breast is fully contained in the bra cup. If the breast are forced toward the sides or center, the bra cup is too small. The center seam should lie against the breastbone. Unless there is a cavity in the chest wall, there should be a "thumbtack" fit in the center of the cups at the chest wall. If the cup is not filled or has wrinkles, a smaller or contoured cup may be the answer. Have the client try on other styles. If flesh overflows, suggest a larger cup or a style with more coverage. The underarm area should lie smooth without cutting into the flesh. If the cup is not filled out, try on a smaller cup or lightly lined style. The bra band should fit snugly, but not too tightly, i.e., you should see an indentation of the band in the skin. If you can run your finger under the lower band easily, the fit is correct. The bottom of the bra should be straight or slightly lower in back. Avoid any digging into the skin when adjusting for a comfortable position. If two fingers fit snugly between the strap and the shoulder, the bra straps are correctly adjusted. Advise the client on the importance of adjusting her bra straps each time the bra is worn and show her how to adjust the straps. Adjustable shoulder straps are preferable to elastic straps. Ask your client to sit down and take a deep breath to see whether the bra binds. Ask her opinion regarding the bra's comfort and appearance. Over a one-year period, a woman's shape may fluctuate. Surgery and medications may affect weight gain or loss, or the remaining breast may change in size. In order to maintain your client's comfort and image, follow up with her every six months. Invite her to the store for a free consultation so that you can check for the proper bra size and fit. Let her know that a few months can make a difference since body structures change over time.

As previously noted, still other embodiments are contemplated than described. As previously noted, the invention is applicable to other prostheses than breast prostheses, for example, foot and hand prostheses and partial foot or hand prostheses. In such cases, differently-shaped shells could be employed that would better fit a foot or hand.

What is claimed is:

1. A method for fabricating an intermediate casting form for a breast prosthesis for a particular patient, comprising:
   providing a shell having a cup-like shape;
   adding an impression material into the shell;
   placing the shell containing the impression material into a cup of a bra that corresponds to where the breast prosthesis is desired;
   fitting the bra onto the patient;
   allowing the impression material to begin to set when contacting a chest wall portion of the patient to form an initial shape; and
   manually altering the initial shape to make an intermediate shape by applying pressure to the impression material before the impression material is permanently unalterable.

2. The method of claim 1, further comprising the step of allowing the impression material to set further when substantially in the intermediate shape.

3. The method of claim 1, further comprising removing the shell and impression material from the bra before the impression material is permanently unalterable, wherein the manually altering step occurs after the step of removing shell and impression material.

4. The method of claim 1, wherein the impression material has a limited time in which it is alterable.

5. The method of claim 1, wherein the shell tends to assume the cup-like shape when not subject to an external stress and tends to alter its shape when subject to pressure applied by a person.

6. The method of claim 1, wherein the shell comprises a polyethylene-based sheet material.

7. The method of claim 1, wherein the shell has a shell wall with a thickness of approximately 1 to 8 mm.

8. The method of claim 1, wherein the shell has a shell wall with a thickness of approximately 1 to 4 mm.

9. The method of claim 1, wherein the impression material has a composition that, prior to setting, is elastomeric.

10. The method of claim 1, wherein the impression material has a composition that is elastomeric following setting of the impression material.

11. The method of claim 1, wherein the impression material is a polyvinylsiloxane putty.

12. The method of claim 1, wherein the bra is one that fits the patient.

13. The method of claim 1, wherein the step of placing the shell occurs prior to the step of placing the bra.

14. The method of claim 1, wherein the manually altering step comprises altering the initial casting form such that the intermediate shape more closely matches a desired shape for the breast prosthesis.

15. The method of claim 1, wherein the step of adding the impression material into the shell comprises adding a sufficient volume of the impression materials such that when the shell and impression material are placed into the bra and the bra is fitted to the patient, a portion of the impression material flows beyond the cup creating an intermediate casting form having at least a partial flange adjacent a breast-like portion of the casting form.

16. The method of claim 1, wherein the method is carried out by at least one of a prosthetic specialist and the patient.

17. The method of claim 1, further comprising enabling the patient view at least one of the initial form and the manually altering step.

18. The method of claim 17, further comprising enabling the patient to affect the manually altering step.

19. The method of claim 17, further comprising taking into consideration input provided by the patient before or during the manually altering step.

20. The method of claim 1, further comprising forcing the impression material against the chest wall with more force than that caused by bra alone, wherein this forcing step is carried out for less time than the impression material is in contact with the chest wall.

21. The method of claim 1, wherein the shell conforms to a shape imposed upon the shell by the intermediate form of the impression material.

22. A method for fabricating a breast prosthesis for a particular patient, comprising:

providing a shell having a cup-like shape;

providing a impression material;

adding the impression material into the shell;

placing the shell containing the impression material into a cup of a bra that corresponds to where the breast prosthesis is desired;

fitting the bra onto the patient;

allowing the impression material to begin to set when contacting a chest wall portion of the patient;

removing the shell and impression material from the bra before the impression material is permanently unalterable wherein the shell and impression material together have an initial shape;

after the step of removing shell and impression material, manually altering the initial shape to make an intermediate shape by applying pressure to the impression material through the shell;

allowing the impression material to set further when substantially in the intermediate shape to create the intermediate casting form for the breast prosthesis;

forming a mold using the intermediate casting form; and filling the mold with a prosthesis material to form the breast prosthesis.

23. The method of claim 22, further comprising placing an artificial nipple/areola onto the breast prosthesis.

24. The method of claim 23, wherein the prosthesis material is more suitable for the breast prosthesis than the impression material.

* * * * *